United States Patent [19]
Clarkson et al.

[11] Patent Number: 6,048,996
[45] Date of Patent: Apr. 11, 2000

[54] INSOLUBLE PROMOTERS FOR NICKEL-CATALYZED HYDROCYANATION OF MONOOLEFINS

[75] Inventors: Lucy Mary Clarkson, Kennett Square, Pa.; Norman Herron, Newark, Del.; William C. Kalb, Lake Charles, La.; Ronald James McKinney, Wilmington, Del.; Edward Francis Moran, Jr., Gibbstown, N.J.

[73] Assignee: E. I. du Pont de Nemours and Company, Wilmington, Del.

[21] Appl. No.: 09/383,898

[22] Filed: Aug. 26, 1999

[51] Int. Cl.⁷ .................................................. C07C 253/10
[52] U.S. Cl. .............................................................. 558/338
[58] Field of Search ................................................ 558/338

[56] References Cited

U.S. PATENT DOCUMENTS 5,512,695   4/1996   Kreutzer et al. ......................... 558/338

*Primary Examiner*—Johann Richter
*Assistant Examiner*—Joseph Murray

[57] ABSTRACT

An improved process for converting an acylcic monoolefin to its corresponding terminal organonitrile by reacting the monoolefin with hydrogen cyanide in the presence of zero-valent nickel, a phosphite ligand, and an insoluble Lewis acid promoter.

15 Claims, No Drawings

INSOLUBLE PROMOTERS FOR NICKEL-CATALYZED HYDROCYANATION OF MONOOLEFINS

BACKGROUND OF THE INVENTION

This invention relates to a process for converting an acyclic monoolefin to its corresponding terminal organonitrile compound by reacting the monoolefin with hydrogen cyanide (HCN) in the presence of zero-valent nickel, a phosphite ligand, and a Lewis acid promoter.

Hydrocyanation catalyst systems, particularly pertaining to the hydrocyanation of olefins, are well known in the art. For example, systems useful for the hydrocyanation of butadiene to form pentenenitrile (PN) and for the subsequent hydrocyanation of pentenenitrile (PN) to form adiponitrile (ADN), are known in the commercially important nylon synthesis field. The hydrocyanation of olefins using transition metal complexes with monodentate phosphite ligands is well documented in the prior art. See for example U.S. Pat. No. 3,496,210, 3,631,191, 3,655,723 and 3,766,237; and Tolman, C. A.; McKinney, R. J.; Seidel, W. C.; Druliner, J. D.; and Stevens, W. R.; Advances in Catalysis, 33, 1, 1985. The hydrocyanation of activated olefins, such as conjugated olefins (e.g., butadiene and styrene) and strained olefins (e.g., norbornene), proceeds without the use of a Lewis acid promoter, while hydrocyanation of unactivated olefins, such as 1-octene and 3-pentenenitrile, requires the use of a Lewis acid promoter. Teachings regarding the use of a promoter in the hydrocyanation reaction appear, for example, in U.S. Pat. No. 3,496,217. This patent discloses an improvement in hydrocyanation using a promoter selected from a large number of soluble metal cation compounds. U.S. Pat. No. 3,496,218 discloses a nickel hydrocyanation catalyst promoted with various boron-containing compounds, including triphenylboron and alkali metal borohydrides. U.S. Pat. No. 4,774,353 discloses a process for the preparation of dinitriles, including ADN, from unsaturated nitrites, including PN, in the presence of a zerovalent nickel catalyst and a triorganotin catalyst promoter. U.S. Pat. No. 4,874,884 discloses a process for producing ADN by the zerovalent nickel-catalyzed hydrocyanation of pentenenitriles in the presence of a synergistic combination of promoters selected on the basis of the reaction kinetics of the ADN synthesis. U.S. Pat. Nos. 5,233,058 and 5,286,825 disclose the nickel-catalyzed hydrocyanation of perfluoroalkyl ethylene and other partially fluorinated olefins. U.S. Pat. No. 5,087,723 discloses nickel-catalyzed hydrocyanation of penteneoates. In each of these cases, the catalyst and promoter are dissolved in the reaction medium, providing an essentially homogeneous reaction environment (i.e., everything is soluble). The homogeneous nature of this reaction system makes it difficult to recover the catalyst and promoter for reuse. Whereas practical methods for recovery of nickel catalyst are known (see, for example, U.S. Pat. No. 3,773, 809), recovery of promoters remains a difficult problem. U.S. Pat. No. 3,846,474 discloses that the addition of aluminosilicate zeolites to a nickel-catalyzed zinc chloride-promoted hydrocyanation reaction of 3-penetenenitrile may improve catalyst utility and product distribution.

SUMMARY OF THE INVENTION

The present invention provides a novel hydrocyanation process wherein the promoter is insoluble in the reaction medium and is, therefore, readily separable from the reagents and reaction products by mechanical means such as filtration. The process of the present invention comprises reacting an acyclic monoolefin with HCN in a temperature range of $-25°$ C. to $200°$ C. and in a pressure range of 0.05 to 100 atmospheres in the presence of a nickel catalyst and an insoluble Lewis acid promoter to produce corresponding terminal organonitrile products, and then separating the promoter by mechanical means, such as filtration.

The insoluble promoters of this invention must exhibit Lewis acidity, this acidity being manifested in a theoretical sense by the metal ions' ability to accept donation of an electron pair forming a dative (donor-acceptor) bond (e.g., from a nitrile or pyridine to form a coordination complex). Preferred insoluble promoters may be selected from several classes of materials: (a) polyolefins (such as polystyrene, polyethylene or polypropylene) having metal ions or metal ion complexes covalently bonded to the polyolefin, (b) sulphonate or carboxylate substituted polyolefins having metal ions or metal ion complexes ionically bonded to the polymer, including metal-exchanged perfluorosulphonic acid resins, (c) metal oxides in which the metal ions themselves are the centers of Lewis acidity, and (d) insoluble metal halides, phosphates or sulfates.

DETAILED DESCRIPTION OF THE INVENTION

The present process for hydrocyanating an acyclic monoolefin to form the corresponding nitrile, comprises reacting an acyclic monoolefin with HCN in the presence of a nickel catalyst and an insoluble Lewis acid promoter. Thereafter, the insoluble promoter may be separated from the reaction mixture by mechanical means, such as filtration.

The monoolefins of the process are described by Formula I or III, and the corresponding terminal nitrile compounds produced are described by Formula II or IV, respectively,

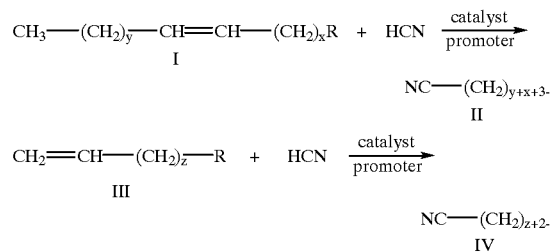

wherein R is H, CN, $CO_2R^2$, or perfluoroalkyl; x is 0 to 12; y is 0 to 12; z is 1 to 12 when R is CN or $CO_2R^2$ and z is 0 to 12 when R is H or perfluoroalkyl; and $R^2$ is $C_1$ to $C_{12}$ straight or branched alkyl.

Preferred monoolefins include 2-, 3- and 4-pentenenitrile, alkyl 2-, 3- and 4-penteneoates, and $CH_2=CH-R^3$, wherein $R^3$ is perfluroalkyl.

Preferred products are adiponitrile, alkyl 5-cyanovalerate, and $R^4-CH_2CH_2CN$, wherein $R^4$ is perfluoroalkyl. Adiponitrile (ADN) is of particular interest because it is an intermediate used in the production of hexamethylenediamine, which, in turn, is used to produce polyhexamethyleneadipamide (nylon-6,6), a commercial polyamide useful in forming fibers, films, and molded articles. Adiponitrile may also serve as a precursor for production of caprolactam by a process involving partial hydrogenation of ADN.

The catalysts employed for this process are zerovalent nickel (Ni(0)) compounds, substantially free of carbon monoxide, which may be preformed or prepared in situ. The catalysts include nickel compounds containing ligands such as phosphines, arsines, stibines, phosphites, arsenites, stibites and mixtures thereof. Ligand may be added in excess of what can theoretically be coordinated to the nickel at a given time. The use of excess ligand often provides improved stability for the nickel catalyst.

A preferred group of these Ni(0) catalysts has the general structure:

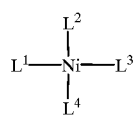

wherein $L^1$, $L^2$, $L^3$, and $L^4$ are neutral ligands which may be the same or different and have the formula P(XYZ) wherein X and Y are selected from the group consisting of R and OR', and Z is OR", wherein R, R', and R" may be the same or different, and wherein R, R', and R" are selected from the group consisting of alkyl and aryl groups containing up to 18 carbon atoms, with aryl being preferred. Alkyl groups may be linear or branched. The term "aryl" is meant to denote an organic radical which is derived from an aromatic hydrocarbon by removal of one atom. Suitable aryl radicals are, for example, phenyl, benzyl, naphthyl, binaphthyl, and anthracenyl.

A particularly preferred group within the foregoing zerovalent nickel catalysts is that disclosed in U.S. Pat. No. 3,903,120, which is incorporated herein by reference. This preferred group of catalysts can be described by the general formula $NiL_4$, where L is a neutral ligand such as a triarylphosphite of the formula $P(OAr)_3$ wherein Ar is an aryl group of up to 18 carbon atoms. Illustrative aryl groups are methoxyphenyl, tolyl, xylyl, and phenyl. Preferred aryl groups are meta-tolyl, para-tolyl, and phenyl, and mixtures thereof.

Another preferred group of zerovalent Ni(0) catalysts consists of compounds of the general formulae shown below:

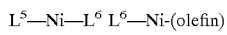

wherein $L^5$ and $L^6$ are bidentate ligands which may be the same or different and have the formula (X)(Y)P—Z'—P(X)(Y), wherein X and Y are selected from the group consisting of R and OR', and Z' has the formula O—R"—O, wherein R, R', and R" may be the same or different, and wherein R, R', and R" are selected from the group consisting of alkyl and aryl groups containing up to 18 carbon atoms, with aryl being preferred, and the olefin contains up to 18 carbon atoms, and is preferably one of the monoolefins being hydrocyanated.

Preferred $L^5$ and $L^6$ are described in U.S. Pat. Nos. 5,512,695, 5,512,696, 5,523,453, 5,543,536, 5,693,843, 5,723,641, 5,821,378, and 5,847,191 and in PCT applications WO9514659, WO9906146, WO9906355, WO9906356, WO9906357, and WO9906358, the disclosures of which are incorporated herein by reference. Especially preferred $L^5$ and $L^6$ are diphosphite ligands illustrated by Ligand formulas A to G below.

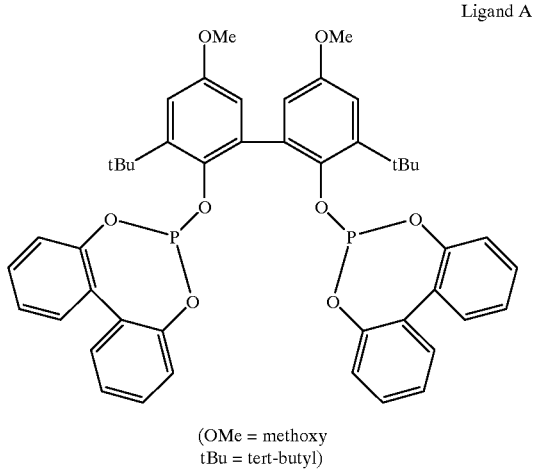

(OMe = methoxy
tBu = tert-butyl)

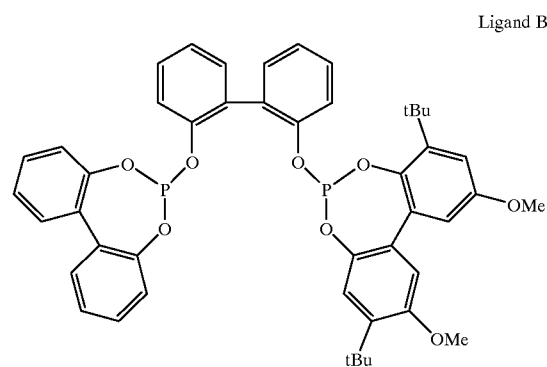

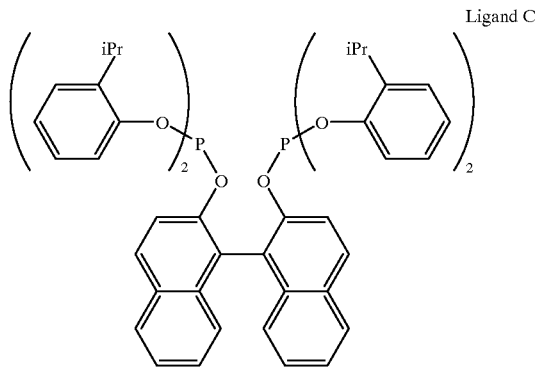

-continued

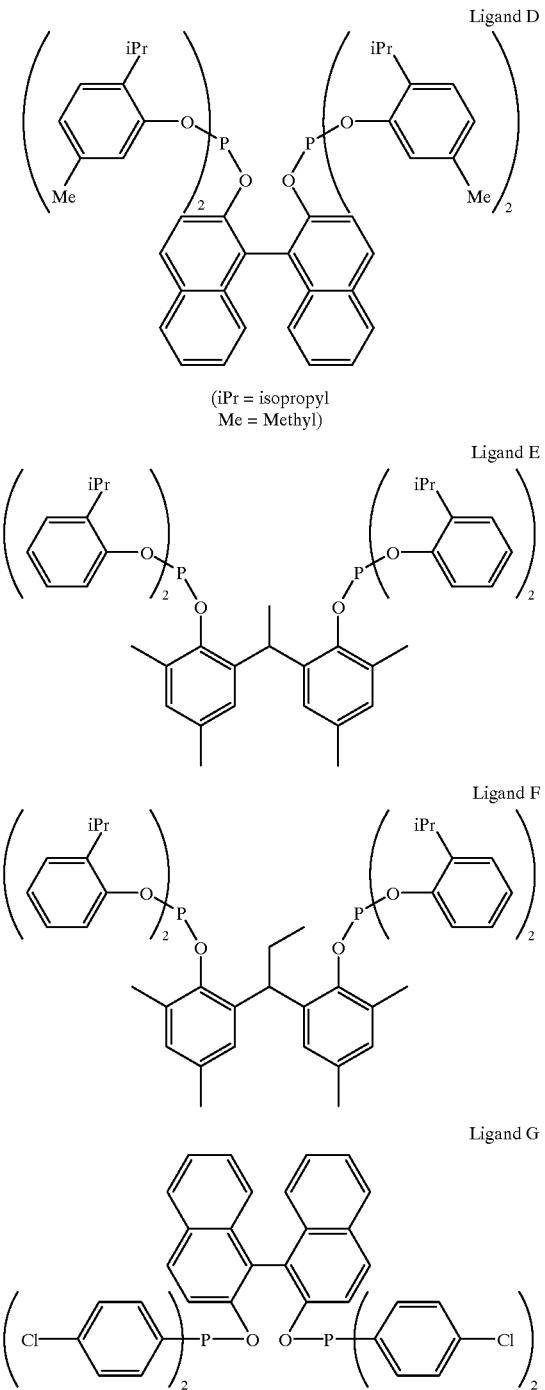

(iPr = isopropyl
Me = Methyl)

The promoters of the present invention must be insoluble in the reaction medium and therefore easily recoverable by mechanical means, such as filtration. The term "insoluble" means that less than about 0.1% of the promoter is dissolved. The insoluble promoters of this invention are not believed to be active as a result of leaching of metal ions from the insoluble promoter into the reaction solution. Analysis of reaction product solutions formed using these promoters indicated metal ion concentrations well below these required for effective promoter activity.

The promoters must have Lewis acidity, as indicated by their ability to coordinate to either a metal-cyanide containing complex or an organonitrile, as measured spectroscopically by a shift in the infrared band assigned to the metal-cyanide or organonitrile stretch upon coordination to the promoter. An example of such a spectroscopically observed shift for a soluble promoter with a nickel-cyanide (Ni—CN) species is described in Advances in Catalysis, Vol. 33 (1985), pages 12–13. Alternatively, Lewis acidity may be measured by spectroscopic measurement of pyridine adsorption onto the insoluble promoters as described by J. A. Lercher, G. Ritter, and H. Vinek, Journal of Colloid and Interface Science, Vol. 106 (1985) pages 215–221.

Insoluble promoters may be selected from among several classes of materials consisting of (a) polyolefins (such as polystyrene, polyethylene or polypropylene) having metal ions or complexes covalently bonded to the polyolefin, (b) sulphonate or carboxylate substituted polyolefins (ion exchange resins) having metal ions or metal ion complexes ionically bonded to the polymer, including metal exchanged perfluorosulphonic acid resins, (c) inorganic metal oxides in which the metal ions themselves are the centers of Lewis acidity, and (d) insoluble metal halides, phosphates or sulfates, including those supported on metal oxides.

Preferred members of class (a) include polystyrene, which may contain varying degrees of cross-linking, in which metal or organometal cations are covalently bonded to an aryl group of the polystyrene. These promoters may be prepared by making a Grignard reagent from p-bromostyrene, reacting the Grignard reagent with a metal or organometal halide to covalently bond the metal or organometal to the styrene group, and then polymerizing the metal-substituted styrene group with or without unsubstituted styrene and cross-linking agents such as divinylbenzene. The metal cation, which may or may not be bonded to other organic groups, is selected from the group consisting of zinc, cadmium, the first transition series (elements 21–29 of the Periodic Table), the second transition series (elements 39–47 of the Periodic Table), the rare earths (elements 57–71 of the Periodic Table), boron, aluminum, gallium, indium, germanium, tin, hafnium, tantalum, tungsten, and rhenium. Preferred metal cations are selected from the group consisting of zinc, aluminum, titanium, manganese, aluminum and tin. Preferred promoters are poly(styrene-Ph—Y)X, wherein Ph is phenyl, Y is $Sn(R)_2$ wherein R is alkyl, aryl, or Cl, and X is a weakly coordinating counterion such as $Cl^-$, $Br^-$, $RSO_3^-$ (wherein R is aryl, alkyl, perfluoralkyl, or perfluoroaryl). Especially preferred promoters are poly(styrene-$Sn(Ph)_2X$), wherein Ph is phenyl and X is a weakly coordinating counterion such as $Cl^-$, $Br^-$, $RSO_3^-$ (wherein R is aryl, alkyl, perfluoralkyl, or perfluoroaryl).

Promoters of class (b) are sulfonated or carboxylated organic polymers known as ion exchange resins, such as polystyrene, in which metal or organometal cations are ionically bonded to the sulfonyl or carboxyl groups. Metal-exchanged perfluorosulphonic acid resins are also members of this class, wherein the metal is Mn, Fe, Co, Zn, La, Ce, Pr, Nd, Sm, Eu, Gd, Tb, Dy, Ho, Er, Tm, Yb, or Lu. (Perfluorosulphonic acid resin is sold under the trademark "Nafion" by E. I. du Pont de Nemours and Company, Wilmington, Del., U.S.A.) Sulfonated or carboxylated polystyrene resins are commercially available under a variety of trade names, for example, "Amberlyst" 21 (sold by Rhom and Haas, Philadelphia, Pa., U.S.A.). These resins may be obtained in acid or ion exchanged forms and the promoters of this invention may be readily prepared by ion exchange. The metal cation, which may or may not be bonded to other organic groups, is selected from the group consisting of zinc, cadmium, the first transition series (elements 21–29), the second transition series (elements 39–47), the rare earths (elements 57–71), boron, aluminum, gallium, indium, germanium, tin, hafnium, tantalum, tungsten, and rhenium. Preferred metal cations are selected from the group consisting of zinc, aluminum, titanium, manganese, aluminum and tin. Particularly preferred promoters are metal or organometal exchanged poly(styrene-$SO_3^-$) resins. Especially preferred is poly(styrene-$SO_3^-Sn(Ph)_3$), wherein Ph is phenyl.

Promoters of class (c) are metal oxides in which the metal ions themselves are the centers of Lewis acidity, this acidity being manifested by the metal ions' ability to accept an electron pair forming a dative (donor-acceptor) bond (e.g., from a nitrile or pyridine to form a coordination complex). Such promoters may be selected from the class consisting of crystalline silicoaluminate clays in their acid forms. Clays such as the natural mineral compositions pyrophyllite, micas, vermiculites or smectites and synthetic clays such as laponite may be used. Essentially amorphous silicoaluminates, with a Si/Al ratio ranging from 10 to 0.05, either native or treated with chloride, sulphate or phosphate to enhance the surface acidity, may be used. The following may also be used: large pore silicoaluminate zeolites (greater than about 8 Angstrom pore size), alumina, hydrous zirconia, zirconia, and zirconia whose surface has been treated with sulfate ion rendering it superacidic; niobic acid and hydrous niobia, acidic gamma alumina, tungstic acid, chromia, molybdic acid, hydrous titania, zinc oxide, iron(III) oxide, lanthanum oxide, heteropolyacids, magnesia/alumina, aluminophosphates, non-Si/Al zeolite-type materials such as ALPOs (crystalline, microporous aluminum phosphate structures), SAPOs (silica-aluminophosphates where silicon ions occupy some of the aluminum sites in a crystalline alumino-phosphate structure), MeAPOs (metal ions such as Co, Mn etc., substituted onto the Al sites of crystalline aluminosilicates), conventional zeolites in which Al is substituted by Ga, B, or Fe, plain or sulfated forms of $SnO_2$ and $HfO_2$, boric acid and boron-containing solid compositions that present surface coordination sites at boron atoms. Any of these suitable promoters may be dispersed onto a high surface area (>20 $m^2$/gm) support such as silica, alumina or carbon. Members of this class are most effective when calcined to remove water and Bronsted (protonic) acid sites. Such calcination requires heating in flowing air to temperatures in excess of 400° C.

Class (d) promoters of this invention consist of a metal cation with an anion which renders it insoluble in the reaction medium, the anion being selected from the class consisting of halide, sulfate and phosphate. Preferred members of this class are metal fluorides and metal fluorides supported on silicoaluminates, iron phosphates, zinc sulfates and iron sulfates and zirconium hydrogen phosphate. Especially preferred members of this class are $AlF_3$, $ZnF_2$, and $SbF_5$ on aluminosilicate. Any of these suitable promoters may be dispersed onto a high surface area (>20 $m^2$/gm) support such as silica, alumina or carbon.

The present hydrocyanation process may be carried out by charging a reactor with all of the reactants, or, preferably, by charging the reactor with the catalyst precursor or catalyst components, the aliphatic monoolefin, the promoter and the solvent to be used and adding the hydrogen cyanide slowly. HCN may be added to the reaction as vapor or liquid, or released to the system utilizing cyanohydrin. See, for example, U.S. Pat. Nos. 3,655,723 and 5,107,012 which are incorporated herein by reference. The reactor may also be charged with the catalyst, promoter, and the solvent to be used, and both monoolefin and HCN added slowly to the reaction mixture. The molar ratio of monoolefin to catalyst may be from about 10:1 to 2000:1. The insoluble promoter is generally present in the range of about 0.1 wt % to 50 wt % of the reaction mass. Preferably the insoluble promoter is present in the range of about 1 wt % to 25 wt % of the reaction mass.

The hydrocyanation reaction can be carried out with or without a solvent. The solvent should be liquid at the reaction temperature and pressure and inert towards the acyclic monoolefin and the catalyst. Generally, such solvents are hydrocarbons such as benzene or xylene, or nitriles such as acetonitrile or benzonitrile. In some cases, the acyclic monoolefin to be hydrocyanated may serve as the solvent.

The reaction temperature is dependent to a certain extent on the particular catalyst being used, the particular monoolefin being used and the desired reaction rate. Generally, temperatures of from −25 to 200° C. can be used, with from 0 to 150° C. being preferred.

Atmospheric pressure is satisfactory for carrying out the present process, and hence pressures of from about 0.05 to 100 atmospheres are preferred for economic reasons.

Preferably, the reaction medium is agitated, such as by stirring or shaking. The reaction may be run either batchwise or in a continuous manner. The promoter may be recovered for further use by mechanical means such as filtration, decantation or centrifugation. The cyanated product can be recovered by conventional techniques, such as distillation.

EXAMPLES

The following nonlimiting examples illustrate the invention. As used herein, "m,p-TTP" refers to tritolylphosphite which contains a mixture of meta- and para-tolyl groups. PNs refers to a mixture of 3-pentenenitrile and 4-pentenenitrile. ADN refers to adiponitrile, MGN to methylglutaronitrile, and ESN to ethylsuccinonitrile.

Example 1

Illustrates That $Fe_2O_3$ (Class C) Promotes Hydrocyanation of PNs to ADN

Under nitrogen, a portion (21.58 g) of a mixture of Ni(m,p-TTP)$_4$ (23.72 g)(the catalyst), m,p-TTP (4.665 g)(excess ligand) and PNs (95.5 g)(acyclic monoolefin) was added to a flask containing $Fe_2O_3$ (0.180 g)(insoluble promoter). The $Fe_2O_3$ formed a slurry in this mixture. The flask and its contents were heated to 60° C. HCN vapor was introduced to the flask by sparging $N_2$ through a chilled trap (0° C.) and into the flask. Liquid samples were withdrawn at 45 minutes, 2, and 3 hours. Infrared analyses showed HCN concentrations to be 385, 640, and 973 ppm at each of these times respectively. The reaction was stopped at the end of 4 hours, and the product, analyzed by gas chromatography (GC), contained 24.53 wt % ADN, 5.77 wt % MGN, and 0.84 wt % ESN. Distribution: 78.7% ADN (the Distribution was obtained by dividing the wt % ADN by the sum of the wt % of ADN, MGN, and ESN).

Example 2

Illustrates That $Fe_2O_3$ is Acting as a Insoluble Promoter $Fe_2O_3$ (0.216 g) was incubated with 30 mL of a catalyst mixture of the same composition used in Example 1 above. The mixture was stirred under nitrogen for 40 hours at 40° C., and 1 hour at 60° C. The mixture was filtered (syringe filter), and the filtrate was transferred to the same hydrocyanation apparatus used in Example 1. Hydrogen cyanide was introduced, as in Example 1, but for a period of only one hour. ADN (0.54 wt %) was formed. A control experiment, using only the same catalyst mixture, but without prior incubation with $Fe_2O_3$, and without other added promoters, was reacted, in the same apparatus, with hydrogen cyanide for 1 hour. In the control experiment, only 0.32 wt % ADN was formed. In Example 1, in which $Fe_2O_3$ is present during the HCN reaction, 2.18 wt % ADN was formed after only 45 minutes, showing that $Fe_2O_3$ acts as an insoluble promoter of the PN to ADN reaction.

Example 3

Illustrates That $Fe_2O_3$ is Not a Catalyst for Hydrocyanation $Fe_2O_3$ (0.036 g) was mixed with PNs (4.0 mL). Liquid HCN (0.40 mL) was added to the mixture, which was then heated to 60° C. for a period of 2 hours. No ADN was detected by GC.

Example 4

Illustrates That a Soluble Promoter Does Not Form When $Fe_2O_3$ Reacts With HCN During Hydrocyanation Two reactors were set up. Reactor 1 contained the same charge as in Example 1 and 0.180 g $Fe_2O_3$. Reactor 2 was empty. Both reactors were heated to 60° C. and HCN flow was started to reactor 1. After 1 hour, HCN flow was stopped to reactor 1 and nitrogen flow was started. Approximately one half of the contents of reactor 1 were filtered (using a syringe filter) and transferred to reactor 2. HCN flow was started on reactor 2, while $N_2$ flow was maintained on reactor 1. Samples were taken from both reactors at 1 hour (the time of filtration and transfer) and at two hours, the time at which HCN was stopped to reactor 2. The results (Table 1) show no more accumulation of ADN during the second hour in reactor 2 (filtered material, under HCN) than occurred during the second hour of reactor 1 (unfiltered material, under $N_2$).

TABLE 1

| Reactor | Time (h) | ADN, wt % | MGN, wt % | ESN, wt % |
|---|---|---|---|---|
| 1 | 1 | 10.47 | 2.53 | 0.403 |
| 1 | 2 | 12.18 | 3.02 | 0.478 |
| 2 | 1 | 11.51 | 2.87 | 0.479 |
| 2 | 2 | 12.44 | 3.18 | 0.540 |

Examples 5–9

Illustrate the Use of Other Insoluble Promoters

In a manner similar to that described in Example 1, other insoluble promoters were demonstrated to be active insoluble promoters as illustrated in Table 2:

TABLE 2

| Ex. | Compound | Weight, g | Wt % ADN | Distribution |
|---|---|---|---|---|
| 5 | FeO(OH) | 0.182 | 3.12 | 76.8% |
| 6 | $Fe_3(PO_4)_2 \cdot 8H_2O$ | 1.03 | 2.092 | 79.5% |
| 7 | $TiO_2$ | 0.167 | 1.14 | 78.6 |
| 8 | ZnO | 0.170 | 18.24 | 78.6 |
| 9 | $ZrO_2$ (2 hour run) | 0.259 | 1.56 | — |

Examples 10–41

Additional Examples of Insoluble Promoters

The examples in Table 3 utilized bidentate ligands (diphosphites) and were carried out using the following common procedure, unless otherwise noted. Ligands A to G are identified in Table 3 and are described above. In some cases, identified as "recycle", the promoter was isolated after the run and reused in a subsequent run with no further treatment.

A glass reactor fitted with a nitrogen bubbler was charged with 3-pentenenitrile (5 mL; 52 mmol), ligand (see Table 3)(0.28 mmol), (ligand)Ni($C_2H_4$) (0.14 mmol) and promoter (see Table 3 for amount) under inert nitrogen atmosphere. The mixture was heated to temperature (see Table 3) and agitated with a magnetic stirrer. HCN was delivered to the reactor by sparging a source of liquid HCN (cooled to 0° C.) with dry nitrogen (see Table 3 for flow rate) and directing the resulting saturated HCN/$N_2$ mixture into the reactor below the liquid level. Progress of the reaction was monitored by removing aliquots and analyzing by gas chromatography. After 1 hr the reaction was terminated. Results are given in Table 3.

(% PN conv=100×total dinitriles product/initial PN's)

(% ADN distribution=100×ADN/total dinitriles product)

TABLE 3

| Ex | Promoter | Amount grams | Ligan | Temp ° C. | $N_2$ flow | % PN Conv. | % ADN Distribution |
|---|---|---|---|---|---|---|---|
| 10 | Polystyrene-SnPh$_2$(CH$_3$SO$_3$) | 1.0 | A | 70 | 30 | 66 | 92 |
| 11 | recycle 2nd time of same sample | | A | 70 | 30 | 61 | 93 |
| 13 | recycle 3rd time of same sample | | A | 70 | 30 | 51 | 94 |
| 14 | Polystyrene-SnPh$_2$(CF$_3$SO$_3$) | 1.0 | A | 70 | 30 | 73 | 90 |
| 15 | recycle 2nd time of same sample | | A | 70 | 30 | 62 | 90 |
| 16 | recycle 3rd time of same sample | | A | 70 | 30 | 58 | 90 |
| 17 | Polystyrene-SnPh(HSO$_4$)$_2$ | 1.0 | A | 70 | 30 | 6 | 90 |
| 18 | Polystyrene-CH$_2$—SnPhCl$_2$ | 0.3 | A | 70 | 30 | 12 | 77 |
| 19 | Polystyrene-SnPh$_2$(CH$_3$SO$_3$) | 1.0 | D | 50 | 30 | 12 | 90 |
| 20 | Polystyrene-SnPh$_2$(CH$_3$SO$_3$) | 1.0 | C | 50 | 30 | 10 | 89 |
| 21 | Poly (4-styrene-sulfonate) [Ph$_3$Sn] | 0.06 | A | 80 | 30 | 31 | 94 |
| 22 | Ph$_3$Sn Nafionate | 0.06 | A | 70 | 30 | 22 | 81 |

TABLE 3-continued

| Ex | Promoter | Amount grams | Ligand | Temp ° C. | N₂ flow | % PN Conv. | % ADN Distribution |
|---|---|---|---|---|---|---|---|
| 23 | Yb Nafionate | 0.06 | A | 70 | 30 | 21 | 77 |
| 24 | Sulfated zirconia dried 500° C. | 0.5 | A | 70 | 30 | 8 | 77 |
| 25 | Cl-promoted silico-aluminate, | 0.5 | A | 70 | 30 | 46 | 88 |
| 26 | Recycle 2nd time same sample | 0.5 | A | 70 | 30 | 17 | 84 |
| 27 | PO-promoted silico-aluminate, | 0.5 | A | 70 | 30 | 27 | 83 |
| 28 | theta-AlF₃ on silico-aluminate, | 0.5 | A | 80 | 12 | 14 | 83 |
| 29 | theta-AlF₃, pure | 0.5 | A | 80 | 12 | 21 | 77 |
| 30 | Acidic alumina, dried 500° C., | 0.5 | A | 70 | 30 | 10 | 76 |
| 31 | Sulfated zirconia calcined 600° C., | 0.5 | A | 80 | 30 | 11 | 75 |
| 32 | Cl-promoted Si/Al calcined 200° C., | 0.5 | A | 80 | 30 | 29 | 78 |
| 33 | Cl-promoted Si/Al calcined 700° C. | 0.5 | A | 80 | 30 | 37 | 84 |
| 34 | AlPO₄ calcined 600° C., | 0.5 | A | 80 | 30 | 12 | 74 |
| 35 | Montmorillonite clay, calcined 600° | 0.5 | A | 80 | 30 | 27 | 78 |
| 36 | ~4% Ti(OH)₄ on silica, dried 300° C. | 0.5 | A | 80 | 30 | 13 | 74 |
| 37 | ~5% HNbO₃ on silica, dried 300° C. | 0.5 | A | 80 | 30 | 19 | 76 |
| 38 | ~5% Zr(OH)₄ on silica, dried 300° C. | 0.5 | A | 80 | 30 | 18 | 76 |
| 39 | Fe₂O₃ | 0.05 | A | 70 | 15 | 11 | 76 |
| 40 | FeO | 0.5 | A | 70 | 10 | 19 | 73 |
| 41 | Cl-promoted silico-aluminate | 0.5 | C | 80 | 12 | 12 | 86 |

Examples 42–143

A 4 mL reactor equipped with a magnetic stir bar, was charged with 0.025 g of promoter and 0.2 mL of catalyst solution comprised of Ni(COD)₂ (※COD※ is 1,5-cyclooctadiene) (0.038 g; 0.14 mmol), diphosphite ligand (0.42 mmol, see Table 4), 3-pentenenitrile (5 mL; 4.2 g; 51.9 mmol), and Ligand A only, toluene (5 mL) to aid in solubilizing ligand. The reaction mixture was heated to 50° C. and agitated while being exposed to an atmosphere of N₂ containing 35% v/v HCN, generated by passing a stream of dry N₂ through liquid HCN at 0° C. After 1.5 hours the reactor was purged with N₂ and the reaction solution diluted with 3 mL acetone. The liquid phase was analyzed by GC chromatography. Results are presented in Table 4 below.

TABLE 4

| Ex | Promoter | Ligand | % PN Conv | % ADN Distribution |
|---|---|---|---|---|
| 42 | ~4% Ti(OH)₄ on SiO₂ (300° C.) | A | 6.9 | 79.5 |
| 43 | ~5% HNbO₃ on SiO₂ (300° C.) | A | 21.2 | 81.2 |
| 44 | ~5% Zr(OH)₄ on SiO₂ (300° C.) | A | 24.6 | 86.1 |
| 45 | theta-AlF₃ | A | 18.3 | 74.7 |
| 46 | theta-AlF₃ on silicoaluminate | A | 40.0 | 88.0 |
| 47 | Silicoaluminate (600° C./4 h) | A | 72.1 | 87.8 |
| 48 | Acidified silicoaluminate (600° C./4 h) | A | 58.2 | 87.6 |
| 49 | Chloride promoted silicoaluminate (200 | A | 29.7 | 83.1 |
| 50 | Chloride promoted silicoaluminate (700 | A | 58.9 | 87.3 |
| 51 | Phosphate promoted silicoaluminate (700 | A | 61.9 | 87.1 |
| 52 | AlPO₄ (600° C./4 h) | A | 19.2 | 74.5 |
| 53 | Commercial silicoaluminate cracking | A | 66.3 | 88.1 |
| 54 | Acidic g-alumina (500° C.) | A | 0.6 | 80.9 |
| 55 | Boric acid promoted g-alumina | A | 27.5 | 80.9 |
| 56 | ZnO on g-alumina | A | 3.5 | 77.2 |
| 57 | ZnO on SiO₂ granules | A | 3.4 | 75.8 |
| 58 | Sulfated zirconia (600° C./4 h) | A | 23.4 | 75.3 |
| 59 | Sulfated zirconia (500° C./4 h) | A | 23.1 | 76.4 |
| 60 | Acid form of Zeolite Y | A | 20.6 | 76.3 |
| 61 | Acid form of Zeolite mordenite | A | 18.2 | 74.6 |
| 62 | MoO₃ | A | 6.3 | 74.1 |
| 63 | WO₃ | A | 17.2 | 74.0 |
| 64 | La₂O₃ | A | 16.2 | 74.2 |
| 65 | Ba(OTf)₂ | A | 18.3 | 75.0 |
| 66 | K10 Montmorillonite (200° C.) | A | 0 | |
| 67 | K10 Montmorillonite (400° C.) | A | 0.1 | |
| 68 | K10 Montmorillonite (600° C./6 h) | A | 49.0 | 84.1 |
| 69 | K10 Montmorillonite (800° C.) | A | 40.1 | 85.4 |
| 70 | Al Montmorillonite | A | 36.1 | 86.5 |
| 71 | Al Laponite | A | 23.0 | 78.0 |
| 72 | Na-Montmorillonite (500° C.) | A | 26.6 | 76.4 |
| 73 | Al-Montmorillonite (500° C.) | A | 11.2 | 87.6 |
| 74 | Zn-Montmorillonite (500° C.) | A | 15.7 | 84.8 |
| 75 | Zn-Montmorillonite (200° C.) | A | 16.9 | 84.4 |
| 76 | 100-Al-Montmorillonite (500° C.) | A | 16.0 | 87.8 |
| 77 | 100-Al-Montmorillonite (700° C.) | A | 35.8 | 86.5 |
| 78 | 100-Zn-Montmorillonite (500° C.) | A | 1.5 | |
| 79 | 100-Zn-Montmorillonite (700° C.) | A | 4.8 | 87.0 |
| 80 | ~4% Ti (OH)₄ on SiO₂ (300° C.) | C | 5.4 | 85.2 |
| 81 | ~4% Ti (OH)₄ on SiO₂ (500° C.) | C | 8.1 | 84.0 |
| 82 | ~5% HNbO₃ on SiO₂ (300° C.) | C | 4.0 | 83.8 |
| 83 | ~5% HNbO₃ on SiO₂ (500° C.) | C | 6.6 | 81.8 |
| 84 | ~5% Zr(OH)₄ on SiO₂ (300° C.) | C | 5.9 | 85.0 |
| 85 | ~5% Zr(OH)₄ on SiO₂ (500° C.) | C | 7.9 | 82.3 |
| 86 | theta-AlF₃ | C | 3.8 | 78.6 |
| 87 | theta-AlF₃ on silicoaluminate | C | 5.3 | 82.8 |
| 88 | Silicoaluminate (600° C./4 h) | C | 13.0 | 85.8 |
| 89 | Acidified silicoaluminate (600° C./4 h) | C | 11.9 | 85.0 |
| 90 | Chloride promoted silicoaluminate (200 | C | 6.5 | 82.0 |
| 91 | Chloride promoted silicoaluminate (700 | C | 9.6 | 84.9 |
| 92 | Phosphate promoted silicoaluminate (700 | C | 6.3 | 82.2 |
| 93 | AlPO₄ (600° C./4 h) | C | 3.0 | 82.5 |
| 94 | Commercial silicoaluminate cracking | C | 44.8 | 85.0 |
| 95 | Acidic g-alumina (500° C.) | C | 0.7 | 61.1 |
| 96 | Boric acid promoted g-alumina | C | 4.6 | 79.1 |
| 97 | ZnO on g-alumina | C | 3.9 | 74.3 |
| 98 | ZnO on SiO₂ granules | C | 16.0 | 84.8 |
| 99 | Sulfated zirconia (600° C./4 h) | C | 3.1 | 76.5 |
| 100 | Sulfated zirconia (500° C./4 h) | C | 4.8 | 80.0 |
| 101 | Acid form of Zeolite Y | C | 5.8 | 80.2 |
| 102 | Acid form of Zeolite mordenite | C | 3.5 | 76.8 |
| 103 | MoO₃ | C | 1.1 | 64.7 |
| 104 | WO₃ | C | 2.8 | 75.4 |
| 105 | La₂O₃ | C | 2.7 | 75.2 |
| 106 | Ba(OTf)₂ | C | 4.24 | 79.3 |
| 107 | K10 Montmorillonite (200° C.) | C | 6.7 | 82.6 |
| 108 | K10 Montmorillonite (400° C.) | C | 19.3 | 84.5 |
| 109 | K10 Montmorillonite (600° C./6 h) | C | 49.4 | 85.1 |
| 110 | K10 Montmorillonite (800° C.) | C | 51.8 | 84.8 |
| 111 | Al Montmorillonite | C | 34.8 | 84.7 |
| 112 | Al Laponite | C | 4.7 | 84.0 |
| 113 | Na-Montmorillonite (500° C.) | C | 5.2 | 84.6 |
| 114 | Al-Montmorillonite (500° C.) | C | 58.0 | 85.1 |
| 115 | Al-Montmorillonite (200° C.) | C | 10.5 | 85.2 |

TABLE 4-continued

| Ex | Promoter | Ligand | % PN Conv | % ADN Distribution |
|----|----------|--------|-----------|--------------------|
| 116 | Zn-Montmorillonite (500° C.) | C | 55.4 | 85.7 |
| 117 | Zn-Montmorillonite (200° C.) | C | 20.7 | 85.6 |
| 118 | Fe-Montmorillonite (500° C.) | C | 21.6 | 85.2 |
| 119 | Fe-Montmorillonite (200° C.) | C | 36.4 | 85.3 |
| 120 | 100-Al-Montmorillonite (500° C.) | C | 14.0 | 84.1 |
| 121 | 100-Al-Montmorillonite (700° C.) | C | 48.5 | 84.6 |
| 122 | 100-Zn-Montmorillonite (500° C.) | C | 4.9 | 78.2 |
| 123 | 100-Zn-Montmorillonite (700° C.) | C | 18.3 | 83.4 |
| 124 | ~4% Ti (OH)$_4$ on SiO$_2$ (300° C.) | D | 3.1 | 73.7 |
| 125 | ~5% HNbO$_3$ on SiO$_2$ (300° C.) | D | 2.0 | 74.5 |
| 126 | ~5% Zr(OH)$_4$ on SiO$_2$ (300° C.) | D | 2.3 | 75.6 |
| 127 | theta-AlF$_3$ | D | 3.0 | 73.4 |
| 128 | theta-AlF$_3$ on silicoaluminate | D | 2.4 | 75.4 |
| 129 | Silicoaluminate (600° C./4 h) | D | 3.3 | 76.3 |
| 130 | Acidified silicoaluminate (600° C./4 h) | D | 2.8 | 75.1 |
| 131 | Chloride promoted silicoaluminate (200 | D | 2.6 | 72.4 |
| 132 | Chloride promoted silicoaluminate (700 | D | 5.3 | 80.6 |
| 133 | Phosphate promoted silicoaluminate (700 | D | 3.2 | 76.8 |
| 134 | AlPO$_4$ (600° C./4 h) | D | 2.7 | 69.9 |
| 135 | Commercial silicoaluminate cracking | D | 3.7 | 83.6* |
| 136 | Acidic g-alumina (500° C.) | D | 0.3 | 49.8 |
| 137 | Sulfated zirconia (600° C./4 h) | D | 3.5 | 74.0 |
| 138 | Sulfated zirconia (500° C./4 h) | D | 3.3 | 73.9 |
| 139 | K10 Montmorillonite (200° C.) | D | 1.46 | 35.9* |
| 140 | K10 Montmorillonite (400° C.) | D | 1.64 | 40.8* |
| 141 | K10 Montmorillonite (600° C./6 h) | D | 4.7 | 83.5* |
| 142 | K10 Montmorillonite (800° C.) | D | 4.4 | 65.9* |
| 143 | Al Montmorillonite | D | 1.5 | 72.4* |

Ligand D: 250 uL, 50 mg promoter. Not corrected for 2M3 contribution to MGN
* Ligand D: 200 uL, 25 mg promoter. Corrected for MGN contribution
100-E-Montmorillonite series—totally exchanged Montmorillonites

Example 144

A 25 mL reactor was charged with 0.058 g Ni(COD)$_2$, 0.559 g Ligand C, 0.75 g K10 Montmorillonite calcined at 500° C. for 4 hours and 7.5 mL 3-pentenenitrile. The reaction mixture was heated to 50° C. and agitated vigorously while a continuous stream of N$_2$ containing 35% v/v HCN was passed through the reactor at a rate of 25 mL/min. After 1.5 hours, the solution phase was diluted with acetone and analyzed by GC chromatography. 60.7% conversion of pentenenitriles, 85.0% selectivity to adiponitrile.

Examples of the Preparation of Class (c) Heterogeneous Promoters for Hydrocyanation

Example 145

H-Montmorillonite Clay 5 g commercial montmorillonite clay (K-10, Aldrich) was slurried into a solution of 5 g ammonium nitrate in 100 mL water. After stirring overnight the solid was collected by filtration, washed with water and suction dried. The wet filter cake was then calcined in flowing air by ramping to 600° C. over 1 hour and held there for 4 hours. The sample was flushed with nitrogen and taken into a nitrogen filled dry-box for collection and storage.

Example 146

Silicoaluminate 5 g commercial silicoaluminate cracking catalyst grade 979 (W. R. Grace) was calcined in flowing air by ramping to 600° C. over 1 hour and holding for 4 hours. The sample was flushed with nitrogen and taken into a nitrogen filled dry-box for collection and storage.

Example 147

Chloride Promoted Silicoaluminate 5 g commercial silicoaluminate powder was slurried into 50 mL water. The pH was adjusted to 1 with HCl and the slurry stirred for 30 mins. The slurry was then evaporated to dryness under reduced pressure. The recovered powder was calcined in flowing air by ramping to 700° C. over 1 hour and holding for 2 hours. The sample was flushed with nitrogen and taken into a nitrogen filled dry-box for collection and storage.

Example 148

Phosphate Promoted Silicoaluminate 5 g commercial silicoaluminate powder was slurried into 50 mL water. The pH was adjusted to 1 with 85% phosphoric acid and the slurry stirred for 30 mins. The slurry was then evaporated to dryness under reduced pressure. The recovered powder was calcined in flowing air by ramping to 700° C. over 1 hour and holding for 2 hours. The sample was flushed with nitrogen and taken into a nitrogen filled dry-box for collection and storage.

Example 149

Sulfate-treated Zirconia 5 g zirconium hydroxide was placed on a frit and 75 mL 0.5M sulfuric acid was poured through the bed and allowed to drain slowly. The solid was suction dried and then calcined in flowing air by ramping to 500° C. over 1 hour and holding for 2 hours. The sample was flushed with nitrogen and taken into a nitrogen filled dry-box for collection and storage.

Example 150 theta-AlF$_3$ 5 g Collidinium tetrafluoroaluminate (Herron et al. J.Amer.Chem.Soc, 1993, 115, 3028) was calcined in flowing air by ramping to 350° C. over 1 hour and holding for 1 hour. The sample was flushed with nitrogen and taken into a nitrogen filled dry-box for collection and storage.

Example 151

Zinc Oxide on Silica 5 g gamma alumina was stirred into a solution of 2 g zinc nitrate in 25 mL water. After 30 mins the solution was evaporated to dryness under reduced pressure and the recovered solid was calcined in flowing air by ramping to 350° C. over 1 hour and holding for 4 hours. The sample was flushed with nitrogen and taken into a nitrogen filled dry-box for collection and storage.

Comparative Examples 1–4

The following comparative examples illustrate that small pore aluminosilicate Zeolites 3A and 4A utilized in U.S. Pat. No. 3,846,474, examples 5 and 6, do not perform as promoters for the nickel-catalyzed hydrocyanation of 3-pentenenitrile.

Comparative Example 1

A reactor was charged with Ni(tritolylphosphite)$_4$ (0.49 g; 0.34 mmol), ZnCl$_2$ (0.095 g; 0.67 mmol) and 3-pentenenitrile (10 mL; 8.4 g; 104 mmol). The reaction mixture was maintained at 25° C. while introducing HCN at a rate of 20 mmol/hr over a period of 16 hrs. Analysis of the resulting product solution by GC showed 3-pentenenitrile conversion of 14% and ADN distribution of 78%. When the reaction was repeated without ZnCl$_2$, less than 0.4% 3-pentenenitrile conversion resulted.

Comparative Example 2

Hydrocyanation of 3-pentenenitrile was carried out in a manner similar to Comparative Example 1 except that 0.90 g of 3A Molecular Sieves (an aluminosilicate Zeolite) were added to the mixture. Analysis of the resulting product solution by GC showed 3-pentenenitrile conversion of 24% and ADN distribution of 80%. When the reaction was repeated without the ZnCl$_2$, less than 0.2% 3-pentenenitrile conversion resulted.

Comparative Example 3

A reactor was charged with Ni(tritolylphosphite)$_4$ (0.49 g; 0.34 mmol), tritolylphosphite (0.59 g; 1.7 mmol), ZnCl$_2$ (0.095 g; 0.67 mmol) and 3-pentenenitrile (10 mL; 8.4 g; 104 mmol). The reaction mixture was maintained at 25° C. while introducing HCN at a rate of 120 mmol/hr over a period of 4.5 hrs. Analysis of the resulting product solution by GC showed 3-pentenenitrile conversion of 5% and ADN distribution of 78%. When the reaction was repeated without ZnCl$_2$, less than 0.4% 3-pentenenitrile conversion resulted.

Comparative Example 4

Hydrocyanation of 3-pentenenitrile was carried out in a manner similar to Comparative Example 3 except that 0.95 g of 4A Molecular Sieves (an aluminosilicate Zeolite) were added to the mixture. Analysis of the resulting product solution by GC showed 3-pentenenitrile conversion of 19% and ADN distribution of 81%. When the reaction was repeated without the ZnCl$_2$, less than 0.2% 3-pentenenitrile conversion resulted.

What is claimed:

1. A process for converting an acyclic monoolfin to its corresponding terminal organonitrile by reacting the monoolefin with HCN, at a temperature of −25° C. to 200° C. and a pressure of 0.05 to 100 atmospheres, in the presence of a zerovalent nickel compound, a phosphorous-containing ligand and an insoluble Lewis acid promoter selected from the group consisting of
   (1) an aryl-group containing polystyrene having metal cations covalently bound to the aryl groups, the metal cations being selected from the group consisting of zinc, cadmium, the first transition series (elements 21–29 of the Periodic Table), the second transition series (elements 39–47 of the Periodic Table), the rare earths (elements 57–71 of the Periodic Table), boron, aluminum, gallium, indium, germanium, tin, hafnium, tantalum, tungsten, and rhenium,
   (2) a sulphonated or carboxylated polystyrene having metal cations ionically bound to the sulphonate or carboxylate groups, the metal cations being selected from the group consisting of zinc, cadmium, the first transition series (elements 21–29 of the Periodic Table), the second transition series (elements 39–47 of the Periodic Table), the rare earth metals (elements 57–71 of the Periodic Table), boron, aluminum, gallium, indium, germanium, tin, hafnium, tantalum, tungsten, and rhenium,
   (3) a metal oxide selected from the group consisting of crystalline silicoaluminate clays or large pore zeolites having a pore size greater than about 8 Angstroms in their acid forms; substantially noncrystalline silicoaluminates, optionally promoted with chloride, sulfate or phosphate; zirconia and sulfate; niobic acid; acidic gamma-alumina; tungstic acid; molybdic acid; hydrous titania; zinc oxide; iron(III) oxide; and lanthanum oxide,
   (4) a metal-exchanged perfluorosulphonic acid resin, wherein the metal is Mn, Fe, Co, Zn, La, Ce, Pr, Nd, Sm, Eu, Gd, Tb, Dy, Ho, Er, Tm, Yb, or Lu,
   (5) a metal cation with an anion which renders it insoluble in the reaction, the anion being selected from the group consisting of halide, sulfate and phosphate, provided, however, that if the cation is Zn, then the anion is other than sulfate,
   (6) metal fluorides, metal fluorides supported on a silicoaluminate support, iron phosphates, iron sulfates and zirconium hydrogen phosphate, and
   (7) AlF$_3$, ZnF$_2$, and SbF$_5$ supported on an aluminosilicate support.

2. The process of claim 1 further comprising mechanically separating the insoluble Lewis acid promoter from the monoolefin, HCN, zero-valent nickel compound, lignd and organonitrile.

3. The process of claim 2 wherein the acyclic olefin is selected from the group consisting of CH$_2$=CH(CH$_2$)$_2$R and CH$_3$—(CH$_2$)$_y$—CH=CH—(CH$_2$)$_x$R, wherein:
   R is H, CN, CO$_2$R$^2$, or perfluoroalkyl;
   x is 0 to 12,;
   y is 0 to 12;
   z is 1 to 12 when R is CN or CO$_2$R$^2$ and z is 0 to 12 when R is H or perfluoroalkyl; and
   R$^2$ is an alkyl group containing 1 to 12 carbon atoms.

4. The process of claim 3 wherein the phosphorous-containing ligand is selected from the group consisting of PXYZ and (X)(Y)P—Z'—P(X)(Y), wherein:
   X and Y are independently R$^3$ or OR$^4$;
   Z is OR$^5$;
   Z' is O—R$^6$—O; and
   R$^3$, R$^4$, R$^5$ and R$^6$ are independently alkyl or aryl groups containing 1 to 18 carbon atoms.

5. The process of claim 4 in which the insoluble promoter is the only promoter.

6. The process of claim 4 in which the promoter is an aryl-group containing polystyrene having metal cations covalently bound to the aryl groups, the metal cations being selected from the group consisting of zinc, cadmium, the first transition series (elements 21–29 of the Periodic Table), the second transition series (elements 39–47 of the Periodic Table), the rare earths (elements 57–71 of the Periodic Table), boron, aluminum, gallium, indium, germanium, tin, hafnium, tantalum, tungsten, and rhenium.

7. The process of claim 4 in which the promoter is a sulphonated or carboxylated polystyrene having metal cations ionically bound to the sulphonate or carboxylate groups, the metal cations being selected from the group consisting of zinc, cadmium, the first transition series (elements 21–29 of the Periodic Table), the second transition series (elements 39–47 of the Periodic Table), the rare earth metals (elements 57–71 of the Periodic Table), boron, aluminum, gallium, indium, germanium, tin, hafnium, tantalum, tungsten, and rhenium.

8. The process of claim 4 in which the promoter is a metal oxide selected from the group consisting of crystalline silicoaluminate clays or large pore zeolites having a pore size greater than about 8 Angstroms in their acid forms; substantially noncrystalline silicoaluminates, optionally promoted with chloride, sulfate or phosphate; zirconia and sulfate; niobic acid; acidic gamma-alumina; tungstic acid; molybdic acid; hydrous titania; zinc oxide; iron(III) oxide; and lanthanum oxide.

9. The process of claim 8 in which the promoter is on a support selected from the group consisting of silica, alumina and carbon.

10. The process of claim 4 in which the promoter is a metal-exchanged perfluorosulphonic acid resin, wherein the metal is Mn, Fe, Co, Zn, La, Ce, Pr, Nd, Sm, Eu, Gd, Tb, Dy, Ho, Er, Tm, Yb, or Lu.

11. The process of claim 4 in which the promoter is a metal cation with an anion which renders it insoluble in the reaction, the anion being selected from the group consisting of halide, sulfate and phosphate, provided, however, that if the cation is Zn then the anion is other than sulfate.

12. The process of claim 11 in which the promoter is on a support selected from the group consisting of silica, alumina and carbon.

13. The process of claim 4 in which the promoter is selected from the group consisting of metal fluorides, metal fluorides supported on a silicoaluminate support, iron phosphates, iron sulfates and zirconium hydrogen phosphate.

14. The process of claim 4 in which the promoter is selected from a group consisting of $AlF_3$, $ZnF_2$, and $SbF_5$ supported on an aluminosilicate support.

15. The process of claim 4 in which the promoter is zinc sulfate supported on a support selected from the group consisting of silica, alumina and carbon.

* * * * *